United States Patent [19]

Meryman

[11] Patent Number: 5,629,145
[45] Date of Patent: May 13, 1997

[54] CRYOPRESERVATION OF CELL SUSPENSIONS

[75] Inventor: Harold T. Meryman, Ashton, Md.

[73] Assignee: Organ, Inc., Chicago, Ill.

[21] Appl. No.: 409,525

[22] Filed: Mar. 24, 1995

[51] Int. Cl.$^6$ .................................................... A01N 1/00
[52] U.S. Cl. .................................................... 435/1.3; 435/2
[58] Field of Search ................................... 435/1.3, 2

[56] References Cited

PUBLICATIONS

T. Takahashi et al., "Mechanism of Cryoprotection by Extracellular Polymeric Solutes," Biophys. J., vol. 54, Sep. 1988, pp. 509–518.

T. Takahashi et al., "Extracellular Glass Formation Explains Cryoprotection by Polymers," Jap. J. of Freezing and Drying, vol. 35, 1989, pp. 32–38.

C.F. Högman et al., "Red Blood Cell Preservation in Protein–Poor Media. 2. Studies of Changes in Red Cell Shape During Storage," Haematologia, vol. 13 (1–4), 1980, pp. 135–144.

*Primary Examiner*—George Yeung
*Attorney, Agent, or Firm*—Oliff & Berridge

[57] ABSTRACT

The present invention provides an improved method of cryopreservation of cell suspensions and compositions useful in same wherein only a non-penetrating extracellular cryopreservation polymer is required.

20 Claims, No Drawings

CRYOPRESERVATION OF CELL SUSPENSIONS

FIELD OF INVENTION

The present invention provides compositions and methods for cyropreservation of cell suspensions.

BACKGROUND OF THE INVENTION

Two general procedures are currently available for the frozen preservation of living cell suspension. One requires the addition of high concentration of low molecular weight solutes that penetrate the cells. Although storage can be conducted in mechanical freezers, these storage procedures require specialized equipment and techniques to remove the solutes following thawing. The second utilizes high molecular weight polymers which do not enter the cells plus a lower concentration of penetrating solutes. Post-thaw processing in this case is much simpler but storage must be at very low temperature, usually in liquid nitrogen.

The formation of ice, which is a prime concern in any method of cell cryopreservation, is initiated by ice crystal nuclei. These may be foreign particles, regions of the surface of the container or dissolved molecules that have on their surface an array of hydrophilic residues comparable to the crystal structure of ice and thereby provide a template for the growth of ice. As a solution is supercooled below its nominal freezing temperature, the size of the array necessary to nucleate ice becomes smaller and, for pure water, the size of a critical nucleus approximates random aggregations of water and self-nucleation occurs. The temperature of self-nucleation is generally referred to as the homogeneous nucleation temperature ($T_{hom}$). $T_{hom}$ for pure water is $-40°$ C. Just as the melting point of a solution is lowered by the addition of solutes, $T_{hom}$ is also lowered as the solute concentration increases.

As an aqueous solution is cooled, it becomes increasingly viscous until, at some low temperature, the translational movement of water molecules stops and the solution becomes a glass. This glass transition temperature, $T_g$, rises as the solute concentration is increased. When freezing occurs during cooling, the solute concentration increases as the temperature falls. Experimentally, the equilibrium glass transition temperature is the temperature at which an aqueous solution, in equilibrium with ice, undergoes a second order phase transition from liquid to an amorphous solid. $T_g$ for different solutes are readily measurable, for example, by differential scanning calorimetry (DSC), and can vary from below $-100°$ C. for low molecular weight solutes to above room temperature for some complex polymers.

When a cell suspension is frozen, heterogeneous nuclei in the extracellular solution initiate ice. It is believed that living cells do not contain heterogeneous nuclei. As the ice crystals grow, water is removed from the extracellular solution, thereby increasing its osmolality. This in turn leads to a movement of water from within the cell down the osmotic gradient. As the temperature falls and ice grows, the cell is progressively dehydrated and at some point cell injury results. The nature of the dehydration injury is believed to be the result of membrane stresses leading to membrane rupture. This form of injury can be prevented by the addition of solutes at a multi-molar concentration so that the amount of ice formed is insufficient to result in damaging cell dehydration. Such a solute, to be useful, must be non-toxic at high concentration and must freely penetrate the cell. Both glycerol and dimethylsulfoxide (DMSO) have been used for this purpose. Glycerol is remarkably non-toxic at high concentrations but penetrates cell membranes slowly and is therefore difficult to introduce and remove. Dimethylsulfoxide penetrates rapidly but becomes increasingly toxic as concentrations exceed 1M (about 7%).

The necessary concentration of cryoprotectant can be substantially reduced by accelerating the rate of freezing. Since the movement of water from the cell interior, across the cell membrane and through the intervening solution to the ice crystal is a physical process requiring time, cell dehydration can be minimized by cooling at a rate that provides insufficient time for all freezable water to leave the cell.

This approach contains practical limitations, however, in that the intracellular solution remains dilute and it is more likely that intracellular ice will form. The goal of this method of cryopreservation is to find a cooling rate such that dehydration is insufficient to cause injury but still concentrates the intracellular solution enough to forestall intracellular freezing. For most cells, these two forms of injury overlap and there is no intervening window that avoids injury. It is then necessary to add penetrating cryoprotectants that reduce the amount of extracellular ice formed and thereby reduce cell dehydration, while at the same time increasing the intracellular concentration to make intracellular crystallization less likely. Concentrations of DMSO ranging from 5% to 10% have provided sufficient recovery of platelets and of stem cells to be clinically useful. However, it is undesirable to transfuse the quantities of DMSO involved and removing the DMSO prior to transfusion is inconvenient and results in the loss of cells. Takahashi (Japanese Journal of Freezing and Drying (1989) 35: 32–38) has reported the ability to reduce the amount of DMSO required to 2% when freezing monocytes in the presence of a 20% solution of extracellular polymeric cryoprotectant.

For many years it has been known that certain polymers are cryoprotective. These have included polyvinylpyrrolidone (PVP), dextran, and more recently, hydroxyethyl starch (HES). Since these large molecular weight polymers do not enter the cell, the mechanism by which they confer cryoprotection has been the subject of speculation.

Success of cryopreservation with certain water soluble polymers which do not permeate the cells has been reported for preservation of bacteria, erythrocytes, lymphocytes, platelets, bone marrow cells, fibroblasts, and other cells. Numerous theories have been advanced to explain this phenomenon including that the polymers protect cells by lowering extracellular salt concentrations at subfreezing temperatures just as penetrating cryoprotectants do, or, that the polymers might adsorb to cells and thus protect the membrane in some way. It has also been speculated that during freezing an electrolyte gradient develops from inside to outside the cells causing an electrolyte leakage which relieves osmotic stress. Phagocytosis of the polymers has even been suggested, which would have the effect of converting them into intracellular agents.

None of these hypotheses explains, however, why some polymers are cryoprotectants and others are not. Nor do they explain why low molecular weight non-electrolytes which do not cross the membrane generally fail to protect. They leave unexplained the need for fast warming, a general requirement of polymer cryopreservation, and none explains why polymers at best generally do not protect more than about 75% of the cells from injury, with the possible exception of erythrocytes. With penetrating cryoprotectants, survival routinely exceeds 90%. There continues to be a need, therefore, for cryopreservation compositions and methods which utilize extracellular cryoprotectants that allow for a range of freezing and thawing procedures.

The present invention provides a general mechanism and method of cryopreservation which utilize extracellular non-penetrating polymer solutions to increase the storage survival of cells in suspension. Compositions useful in the disclosed method are also provided.

SUMMARY OF THE INVENTION

The present invention is based on the present inventors' appreciation that extracellular polymers alone can prevent injury from extracellular ice and that the penetrating solutes currently used have been necessary to suppress intracellular ice. The applicants have discovered that a useful temperature range exists between the glass transition temperature of the extracellular polymer solution, as an upper limit, and the temperature of spontaneous freezing of the intracellular solution, as a lower limit, where satisfactory storage of the cell suspension can be achieved in the absence of penetrating cryoprotectant. The absence of a required penetrating cyroprotectant in the method of the present invention eliminates the need for post-thaw treatment, such as would be required to remove a penetrating cryoprotectant, or expensive freezers or liquid nitrogen as the storage temperature will be generally above −40° C. to −50° C.

The present invention provides, therefore, a method of cryopreservation of cell suspensions which broadly includes determining the temperature, $T_{hom}$, of spontaneous freezing of the intracellular solution of a population or subpopulation of cells of interest; choosing a cryoprotectant polymer solution with a glass transition temperature, $T_g$, that prevents excessive cell dehydration during freezing; mixing a cell suspension of the population or subpopulation of cells of interest in an appropriate buffer which contains the cryoprotectant polymer and storing the cell suspension at a temperature, $T_{storage}$, between $T_{hom}$ and $T_g$ such that when the cell suspension is returned to ambient temperature the functional survival of the desired population or subpopulation of cells is sufficent for the specific application.

Once $T_{hom}$ and $T_g$ are determined for a given population of cells and polymer solutions, respectively, the presently disclosed method will allow selection of a range of storage conditions convenient to one of ordinary skill. Accordingly, it is appreciated that optimization of parameters such as storage containers, freezers, storage buffers, freezing rates and warming rates will require but routine experimentation and will, in large part, be dependent on the availability of equipment and convenience of the operator.

This invention provides a method for prolonged shelf-life of cellular products, such as transfusible cellular products, which entails storage at temperatures below 0° C. of cells in a solution of at least one polymeric, non-toxic cryoprotectant which is, preferably substantially free of penetrating cryoprotecting solutes.

The invention provides an improved method for prolonged shelf-life of cellular products, such as transfusible cellular products which includes providing a viscous extracellular medium which reduces the diffusion of water out of cells in the cellular product while ensuring the absence of intracellular ice formation.

The present invention reduces or eliminates the need for penetrating cryoprotectant, controlled rate freezing or rapid rewarming.

This invention significantly improves the procedure for storing red blood cells—without post thaw wash—by providing less cumbersome methods that lead to acceptable red cell morphology and hemolysis and maintenance of adenosine triphosphate (ATP) and 2,3-diposphoglycerate (2,3 DPG) levels at physiological concentrations for extended periods of time.

This invention provides a method which maintains the functional response of cryopreserved platelets such as the response to ADP induced aggregation and commonly measured indicators of metabolic integrity such as plasma pH, $pO_2$, $pCO_2$ and hypotonic shock response, but requires no post-thaw processing as compared to platelets which are cryopreserved with penetrating cryoprotectants.

The present invention also provides a method of cryopreserving cellular biological materials such as allograft tissue for use in graft and transplants, hybridomas, myelomas, permanent cell lines, primary culture lines, transformed cell lines, and genetically engineered cells.

Compositions useful in the presently disclosed method are also disclosed.

DETAILED DESCRIPTION OF THE INVENTION

The present invention provides a method of cryopreservation of cell suspensions. The present inventors have discovered that in the course of cryostorage of cells the presence of an extracellular polymer solution, as extracellular ice forms the extracellular polymer solution is concentrated and some cell dehydration occurs. As the polymer solution is progressively concentrated and cooled, it rapidly becomes viscous and forms an increasing barrier to the diffusion of water from the cell to the ice crystal. At some point the diffusion of water is so slow that cell dehydration effectively ceases and, at some lower temperature, the glass transition temperature of the polymer solution is reached and further movement of water is obviated. Since the intracellular solution contains no heterogeneous nuclei, intracellular ice will not form until the temperature is lowered to $T_{hom}$ where self-nucleation occurs. Depending on the intracellular solution and its concentration, this temperature will be somewhere below −40° C. Below this temperature, ice will be nucleated. Ice growth will be negligible at this temperature but, during thawing, there is ample opportunity for ice crystal growth and cell destruction.

For this reason, current cell freezing procedures, when extracellular polymers are used, require the addition of a penetrating cryoprotectant usually DMSO, at a concentration usually ranging from 2–5%. Lower concentrations are ineffective while higher concentrations become toxic. Although the presence of DMSO will alter the temperature at which water transfer stops, the polymer remains the dominant factor in limiting dehydration. The principle effect of the added DMSO may be to lower the $T_{hom}$ of the intracellular solution so that when nucleation of the intracellular solution does occur, crystal growth will be limited.

There are two problems with this procedure. First, although ice growth may be controlled during cooling, it can occur during rewarming and very rapid rewarming is required to minimize cell injury from intracellular ice. Second, both cooling and rewarming rates are critical in conventional methods. In a sample of significant size, however, uniform cooling and warming rates throughout the sample are impossible and the larger the sample the more difficult it is to rewarm rapidly. Cell recoveries following freezing using this procedure always fall short of 100 percent. The presently disclosed invention is directed to a procedure that provides for superior cell recovery without the use of penetrating cryoprotectant and without the need for controlled rate freezing or rapid rewarming.

In order to obviate the need for controlled rate freezing and, therefore, to circumvent the problems introduced by the inability to cool at a uniform rate throughout the specimen, the presently disclosed method includes the selection of a polymer with a $T_g$ such that optimum recovery is achieved over a wide range of cooling rates. For cells with different surface-to-volume ratios and/or different tolerance to dehydration, the optimum $T_g$ will be different, but decidedly determinable. Blood platelets, for example, are more sensitive to hyperosmotic stress as well as being much smaller than monocytes and require a polymer with a higher $T_g$ for optimum recovery.

Selecting the optimum polymer is only a first step in improving cell recovery after a freeze-thaw cycle. The obstacles of intracellular freezing remain. As Takahashi showed with monocytes, cell recovery was only moderately good even using a polymer with optimum $T_g$ and the addition of DMSO was necessary to raise recovery to 95%. As should be evident from the above description, using conventional techniques it is intracellular freezing which limits recovery when only an extracellular polymer is used and corrected for same with the addition of intracellular cryoprotectant.

The present inventors have discovered that intracellular cryoprotectant is not necessary if the cellular suspension is stored at a temperature above the $T_{hom}$ of the intracellular solution. If the storage temperature is below the glass transition temperature of the extracellular polymer no diffusion of water from the cell can take place and dehydration injury is foreclosed. If the cells contain no heterogenous ice nuclei, no intracellular freezing will take place as long as the temperature is well above $T_{hom}$. The possibility remains that low temperature protein denaturation may take place over time and that ice nucleation induced by the external events such as vibration may induce freezing in individual cells. The feasible storage duration at these intermediate subfreezing temperatures can be determined only by experimentation and the amount of cell loss that is acceptable will depend on the cells involved and the purpose for which they are being preserved. One of ordinary skill in the art will appreciate, however, that the experimentation required for such a determination is routine in the art. Blood platelets, for example, cannot currently be stored longer than five days and losses of 15–25% of the cells does not render them unacceptable for clinical use. Platelets frozen in an acceptable polymer such as HES or a fraction of HES would have great clinical value even if the storage time were limited to a few weeks and losses comparable to those seen after five days of room temperature storage were incurred.

The polymer to be used as cryoprotectant in the presently disclosed method must be selected to have a $T_g$ that is optimum for the particular cell suspension to be cryopreserved. The appropriate $T_g$ will be determined by using a panel of polymers with $T_g$s ranging from about 10° C. to about –40° C., preferable, about 0° C. to about –40° C. When the optimum $T_g$ has been defined, the selection of cryoprotectant will then be on the basis of clinical acceptability, selecting from among all available polymers having the appropriate $T_g$.

Since the intracellular solution will supercool to –40° C. or below before ice is nucleated and since it is the nucleation of ice that creates the problems that have heretofore been partially met by the addition of intracellular cryoprotectants, the presently disclosed method limits storage temperature to temperatures above $T_{hom}$, thereby avoiding ice nucleation and maintaining the intracellular solution in a supercooled state. Some compromises in storage time may result but for many applications this is a reasonable trade-off. Frozen storage of platelets for even a few weeks or months would be of major utility. If only extracellular polymers are used as cryoprotectants, and presuming that the polymer is acceptable for transfusion, no post-thaw processing will be required.

Examples of extracellular polymeric cryoprotectants useful in the presently disclosed method include dextran, hydroxyethyl starch, FICOLL a nonionic synthetic polymer of sugar, such as, "FICOLL" and polyvinyl pyrrolidone. Dextran useful in the present invention may range in molecular weight from 10–500 kD, more specifically, dextran of 10, 40, 250, 450 or 500 kD may be used, as described in Takahasi et al (Biophys J (1988) 54: 509).

These cryoprotectants will normally be used in a solution at a concentration sufficent to assure acceptable survival without being toxic in subsequent use, for example, when transfused. The amount of cryoprotectant used may also be dependent on the type of cells being preserved. Moreover, treatment conditions, such as pre- or post-storage dilution with suitable buffers or cell culture media may be desireable.

In an embodiment in accordance with this invention, blood is drawn from the donor into an anticoagulant such as, but not limited to, CPDA-1, CPD. Following collection of whole blood in the anticoagulant, the red cells are separated from the plasma by, for example, centrifuging the whole blood, at a relatively high force ("hard spin"), such as, but not limited to, about 7268 G for 10 minutes, whereby the red cells are packed at a hematocrit of about 80% or higher. The packed cells are resuspended in a suitable volume of a biologically compatible buffer containing the extracellular polymeric cryoprotectant. The final volume of the cell suspension is selected so that it is comparable to the volumes, typically 350 to 400 ml, conventionally used for storing transfusible red blood cells known to those of skill in the art.

Dilution for such storage may be accomplished by any acceptable means. For example, the polymer solution may be contained in a satelite bag, just as current additive solutions ADSOL or NUTRICEL.

One of ordinary skill will appreciate that for red cell storage, the acceptability of various treatment and storage conditions can be evaluated by pre- and post- storage comparisons of, for example, the morphological index, the percentage of hemolysis, the intracellular pH, and the levels of ATP and 2,3 DPG of the stored cells.

The morphological index may be measured by any method known to those of skill in the art. For example, it can be measured by direct observation of the morphology of paraformaldehyde-fixed cells in the light microscope according to the procedure of Hogman et al (Hogman, C. F., et al (1980) Hematologia 13: 135–144) in which the cells are scored according to the extent to which they depart from normal discoid shape.

The percentage of hemolysis may be measured by any method known to those of skill in the art. For example, samples of cells can be assayed for percent hemolysis with a hemoglobinometer. The levels of ATP and 2,3 DPG may be measured by any method known to those of skill in the art.

In another embodiment of the present invention, platelets are stored in an extracellular polymeric cryoprotectant by methods described above.

The difficulty of preserving platelets for future use without degrading their activity is well recognized in the art. The loss of activity is well documented in the literature.

During platelet preparation, platelets are activated and when stored for several days at room temperature they exhibit a variety of functional and morphological abnormalities including a poor response to aggregating agents and a lowering of the plasma pH. To maintain an acceptable pH during storage it is crucial that sufficient oxygen be able to enter the bag and that $CO_2$ be able to diffuse out. A lack of oxygen entry into the storage container causes platelets to switch from aerobic to anaerobic metabolism with a resultant increase in the production of lactic acid which in turn is accompanied by an increase in pH. Agitation during storage is also considered necessary and although the mechanism behind the impairment of non agitated platelets is not understood, it has been suggested that gas exchange may be of major importance. Storage at 22° C. with continuous aggitation is currently the only licensed method of platelet storage and carries a 5-day shelf life.

The prior art preservation techniques have included the preparation and use of frozen autologous platelets using 5% of either glycerol or dimethyl sulfoxide as cryoprotectant. Cryopreservation has not been generally utilized for storage with the exception of locations which experimentally stockpile matched donor platelets and autologous platelets for leukemia patients. The key issue affecting acceptance is the poor quality and recovery of the platelets after thawing.

The use of dimethyl sulfoxide has not been completely satisfactory because of irreversible changes in the platelets thought to be associated with the toxicity of DMSO.

Cryopreservation of platelets has previously been found to lead to severe reduction in the functional response of these cells. The nature of the defects underlying the deficient function of stored platelets is unclear. However, it is known that the platelets become activated during storage and it is believed that this activation induces the release of platelet ADP (adenosine diphosphate) which can cause irreversible or reversible changes in platelet membranes, thus, rendering them refractory to aggregating agents.

The present invention is expected to provide for extended storage of platelets without the substantial loss of activity during storage which is a characteristic of the currently licensed preservation method. The metabolic integrity as measured by plasma pH, $pO_2$, $pCO_2$ and hypotonic shock response (HRS) is expected to be maintained throughout the storage period.

Accordingly, the present invention is expected to provide a method for the extended preservation of platelets without agitation under cryopreservation temperatures, and which enables the transfusion of the platelets without further processing following thawing.

It is also an object of this invention to provide a composition which has special utility in the preservation of platelets.

In this embodiment of the invention, platelets can be taken from healthy volunteer donors by the use of manual or automated techniques, such as the blood Cell Separator Cobe-Spectra, known to those of ordinary skill. Whole blood can be anticoagulated with acid citrate dextrose (ACD) (1:9) and after passing through the separation belt is divided into platelet concentrates, plasma and red blood cells. During this procedure, the plasma and the red blood cells are reinfused to the donor. The volume of blood proceeds depends on the precount of the platelets, but usually equals 2.5–3.0 liter. Platelet concentrates are continuously transferred to the collection bag to a final volume of 180 ml and centrifuged at 2000×g for 15 min at room temperature. Almost all of the platelet poor plasma is transferred into an empty plastic bag, leaving 45 ml over the platelet pellet. At this point, the cryoprotectant of the presently disclosed invention can be added to the bag containing the platelet pellet and stored in a metal container which is placed horizontally into a freezer, maintained at a temperature in the range of $T_{hom}$ of platelets to $T_g$ for the chosen cryoprotectant.

When the platelets are required for use, the frozen platelets can be removed from the freezer, the metal container is removed and the bag containing the platelet concentrate is placed in a water bath at any temperature between 20° C. and 37° C. After thawing, the platelet suspension can be transfused without further manipulation.

One of ordinary skill will appreciate that for platelet storage, the acceptability of various treatment and storage conditions can be evaluated by pre- and post- storage comparisons of platelet metabolic integrity, such as plasma pH, $pO_2$, $pCO_2$ and hypotonic shock response (HRS).

All publications mentioned or cited above are herein incorporated by reference. The scope of the presently disclosed invention is not to be limited by the above detailed description of certain preferred embodiments. It will be apparent to those skilled in the art that various modifications and equivalents of the disclosed invention can be made without departing from the spirit or scope of the invention.

What is claimed is:

1. A method for cryopreservation of a cell suspension comprising the steps of:
    (a) mixing said cell suspension with a storage solution containing at least one non-penetrating polymer to produce a storage mixture wherein cells in said suspension contain an intracellular solution having a spontaneous intracellular freezing temperature of $T_{hom}$ and said storage solution has a glass transition temperature of $T_g$, and
    (b) maintaining said storage mixture at a temperature above $T_{hom}$ and not more than $T_g$, thereby avoiding ice nucleation and maintaining the intracellular solution in a supercooled state.

2. The method of claim 1 wherein said cell suspension is substantially an erythrocyte cell suspension.

3. The method of claim 1, wherein said cell suspension is substantially a platelet cell suspension.

4. The method of claim 1, wherein said nonpenetrating polymer is hydroxyethyl starch.

5. The method of claim 1, wherein said storage solution comprises a fraction of hydroxyethyl starch.

6. The method of claim 1, wherein said polymer has a $T_g$ in the range of 0° C. to −40° C.

7. The method according to claim 1, wherein said storage mixture is maintained at a temperature range higher than −50° C.

8. The method according to claim 1, wherein said storage mixture is maintained at a temperature range higher than −40° C.

9. The method according to claim 1, further comprising determining said spontaneous intracellular freezing temperature of $T_{hom}$.

10. The method according to claim 1, wherein said storage mixture includes no penetrating cryoprotectant.

11. The method according to claim 1, wherein said at least one nonpenetrating polymer comprises at least one polymer selected from the group consisting of non-ionic synthetic polymers of sugar and polyvinyl pyrrolidone.

12. The method according to claim 1, wherein said at least one nonpenetrating polymer comprises dextran having a molecular weight range from 10–500 kD.

13. The method according to claim 12, wherein said at least one nonpenetrating polymer comprises a polymer selected from the group consisting of dextran of 10, 40, 250, 450 and 500 kD.

14. The method according to claim 3, wherein the maintaining step does not include agitation.

15. The method according to claim 3, further comprising thawing said platelets at a temperature between 20° and 37° C.

16. The method according to claim 1, wherein said storage solution is substantially free of penetrating cryoprotecting solute.

17. The method according to claim 1, wherein said storage solution is substantially free of dimethylsulfoxide.

18. The method according to claim 1, wherein said storage solution is substantially free of glycerol.

19. A method for the cryopreservation of a cell suspension comprising the steps of:
(a) mixing said cell suspension with a storage solution containing at least one non-penetrating polymer to produce a storage mixture wherein cells in said suspension contain an intracellular solution having a spontaneous intracellular freezing temperature of $T_{hom}$ and
(b) maintaining said storage mixture at or below a temperature where dehydration of said cells is effectively ceased, said temperature being higher than $T_{hom}$ thereby avoiding ice nucleation and maintaining the intracellular solution in a supercooled state.

20. The method for the cryopreservation of a cell according to claim 19, wherein said temperature where dehydration of said cells effectively ceases is below 0° C.

* * * * *